(12) United States Patent
Satpute et al.

(10) Patent No.: US 11,029,298 B2
(45) Date of Patent: Jun. 8, 2021

(54) ANALYZER COMPONENT MONITORING

(71) Applicant: Rosemount Inc., Shakopee, MN (US)

(72) Inventors: Suresh S. Satpute, Pune (IN); Sayali P. Gajare, Ambarnath East (IN); Swati S. Patil, Pune (IN)

(73) Assignee: Rosemount Inc., Shakopee, MN (US)

( * ) Notice: Subject to any disclaimer, the term of this patent is extended or adjusted under 35 U.S.C. 154(b) by 336 days.

(21) Appl. No.: 15/448,002

(22) Filed: Mar. 2, 2017

(65) Prior Publication Data

US 2018/0128797 A1 May 10, 2018

Related U.S. Application Data

(63) Continuation of application No. PCT/IN2016/050385, filed on Nov. 4, 2016.

(51) Int. Cl.
*G01N 33/00* (2006.01)
*G01N 30/86* (2006.01)
*G01N 30/02* (2006.01)
*G01N 30/88* (2006.01)

(52) U.S. Cl.
CPC ....... *G01N 33/007* (2013.01); *G01N 30/8651* (2013.01); *G01N 30/8658* (2013.01); *G01N 30/8675* (2013.01); *G01N 33/0073* (2013.01); *G01N 2030/025* (2013.01); *G01N 2030/889* (2013.01)

(58) Field of Classification Search
CPC ............. G01N 33/007; G01N 33/0073; G01N 30/8651; G01N 30/8658; G01N 30/8675; G01N 2030/889
See application file for complete search history.

(56) References Cited

U.S. PATENT DOCUMENTS 8,389,289 B2  3/2013  Kawana
2007/0045190 A1* 3/2007 Li ...................... G01N 30/8665
                                                              210/656
2008/0244437 A1  10/2008  Fischer
(Continued)

FOREIGN PATENT DOCUMENTS

JP    H04-252928    9/1992
JP    2010-066155   10/2011

OTHER PUBLICATIONS

Thermo Electron Corporation, "Successful HPLC Operation, A Troubleshooting Guide—Version 1.1" 2004 (Year: 2004).*
(Continued)

*Primary Examiner* — Paul M. West
(74) *Attorney, Agent, or Firm* — Christopher R. Christensen; Kelly, Holt & Christenson PLLC

(57) ABSTRACT

A gas analyzer includes a sample inlet, a sample outlet, a detector, a monitoring component, and a controller. The sample inlet is configured to receive a sample and is coupled to the sample outlet. The detector is operably disposed between the sample inlet and the sample outlet and is configured to provide an indication relative to the sample. The monitoring component is configured to provide a diagnostic indication regarding at least one component of the gas analyzer. The controller is configured to control flow through the gas analyzer and is operably coupled to the detector to analyze the sample, provide the analysis to the monitoring component, and provide the indication of health to an output.

12 Claims, 8 Drawing Sheets

(56) References Cited

U.S. PATENT DOCUMENTS

2010/0127860 A1* 5/2010 Ganguly ............ G01N 30/8693
340/540
2011/0147312 A1 6/2011 Cunnien et al.
2013/0304393 A1 11/2013 Sutan

OTHER PUBLICATIONS

International Search Report and Written Opinion for International Patent Application No. PCT/IN2016/050385, dated May 16, 2017, 15 pages.
First Office Action dated Apr. 2. 2020 for Chinese Patent Application No. 201710535300.3, 13 pages including English translation.
Extended search Report dated May 14, 2020 for European Patent Appplication No. 16920523.4, 12 pages.
Japanese Office Action dated Jul. 14, 2020 for Japanese Patent Application No. 2019-522730, 17 pages including English translation.
Second Chinese Office Action dated Nov. 26, 2020 for Chinese patent Application No. 2017105353003, 10 pages including English translation.
First Examination Report for Indian Patent Application No. 201927016038 dated Jan. 13, 2021, 7 pages.
Second Final Office Action for Japanese Patent Application No. 2019-522733 dated Feb. 24, 2021, 11 pages including English translation.

* cited by examiner

| Symptoms \ Issues | Column Contamination | Detector Contamination | Defective Detector Filaments | Increase in Column Bleed | Column Broken / Loose Connections | Column Deteriorating | Column Overload | Detector Overload | Column Absorption | Detector Filament Out Of Balance | Dirty/Defective Detector | Detector Power Off | Normal Degradation With Use | Stationary Phase Accumulated In Outlet | Minor Leakage | Major Leakage | Poor Column Installation |
|---|---|---|---|---|---|---|---|---|---|---|---|---|---|---|---|---|---|
| Increase In Retention Time | e | | | | | | | | | | | | | | | | |
| Decrease In retention Time | | | e | | e | | | | | | | | | | | | |
| Retention Time Inconsistent | | | | e | | | | | | | | | | | | | |
| Baseline Noise | e | | e | e | | | | | | | | | | | | | |
| Irregular Baseline Drift When Operated Isothermally | e | | e | e | | | | | | e | | | | | | | |
| Constant Baseline Drift In One Direction | | e | | e | | | | | | | | | | | | | |
| Baseline Cannot Be Zeroed | | | | | | | | | e | | | | | | | | |
| Baseline Wander | e | | | | | | | | | | | | | | | | |
| High Background Signal: Noise | e | | e | e | | | | | | | e | | | | | | |
| Loss Of Resolution | e | | | | e | | | | | | | | e | | | | |
| Abnormal Peak Shape: Tailing Peak | e | | | | | | | | | | | | | | | | |
| Peak Broadening | e | | | | | | | | | | | | | e | | | |
| Ghost Peaks | e | | | | | | | | e | | | | | | | | |
| Missing Peaks | e | | | | | | | | | | | | | | | | |
| Baseline Irregular Shape: Dip After Solvent Peak | | e | | | | | | | | | | | | | | | |
| No Peak After Solvent Peak | | e | | | | | | | | | | | | | | | |
| All Peaks Change In Size | | e | | | | | | | | | | | | | | | |
| Negative Peaks | | e | | | | | | | | | | | | | | | |
| No Peak | | | | e | | | | | | | e | e | | | | | |
| Only One Peak Present | | e | | | | | | | | | | | | | | | |
| Peaks Less Than Standard Number | e | e | | | | | | | | | | | | | | e | |
| Peak More Than Standard Number (Unwanted Peaks) | e | | | | | | | e | e | | | | | | | | |
| Broad Solvent Peaks | | | | e | | | | | | | | | | | | | |
| Unresolved Peaks | | | | | e | | | | | | | | | | | | |
| Fronting Peaks | | | | | | e | | | | | | | | | | | |
| Flat-top Peaks / Rounded Peaks | | | | | | | e | | | | | | | | | | |
| Split Peaks | | | | | | | e | | | | | | | | | | |
| Increase In Peak Width | e | | | | | | e | e | | | | e | e | | | e | |
| Decrease In Peak Width | | | | | | | | | | e | | | | | | | |
| Increase In Peak Height | e | e | | | | | | | | | | | | | | | |
| Decrease In Peak Height | e | e | | | | | | | | | | | | e | | | |
| Increase In Peak Area | e | e | | | | | | | e | | | | | | | | |
| Decrease In Peak Area | e | e | | | | | | | e | | | | | e | | | |
| Increase In TF | e | | | | | e | | | | | | | | | | | |
| Decrease In TF | | | | | | e | | | | | | | | | | | |
| Decrease In RF | | e | e | | | | | | | | | | | | | | |

FIG. 3

ANALYZER COMPONENT MONITORING

BACKGROUND

Analyzers, such as process gas analyzers, laser-based gas analyzers, and gas chromatographs generally receive a sample gas input and convey the gas through a gas measurement stage to provide an analytic output related to some aspect of the sample gas.

Gas chromatography concerns the separation of a mixture of chemical compounds based on migration rates through a chromatograph column. Separation may be based on differences in boiling point, polarity, or molecular size, for example. The separated compounds may then flow across a suitable detector, such as a thermal conductivity detector (TCD), which detects the concentration of each compound present in a given sample. Knowing the concentration of individual compounds makes it possible to calculate certain physical properties of a sample, such as BTU, specific gravity, or other desired properties, using industry standard equations.

Modern gas chromatographs comprise a variety of components and subcomponents, including multiple valves and columns to split up compound separation into several subprocesses. Ensuring that each component is functioning properly is important for accurate chromatography results. For example, over an extended period of time (generally several months to years), contamination in the flow path, or changes to performance of a column, can affect the time required for a component to exit the column.

SUMMARY

A gas analyzer includes a sample inlet, a sample outlet, a detector, a monitoring component, and a controller. The sample inlet is configured to receive a sample and is coupled to the sample outlet. The detector is operably disposed between the sample inlet and the sample outlet and is configured to provide an indication relative to the sample. The monitoring component is configured to provide a diagnostic indication regarding at least one component of the gas analyzer. The controller is configured to control flow through the gas analyzer and is operably coupled to the detector to analyze the sample, provide the analysis to the monitoring component, and provide the indication of health to an output.

BRIEF DESCRIPTION OF THE DRAWINGS

FIG. 3 illustrates one example Component/Symptom Matrix that may be useful in accordance with some embodiments of the present invention.

DETAILED DESCRIPTION OF ILLUSTRATIVE EMBODIMENTS

Figure 1A:
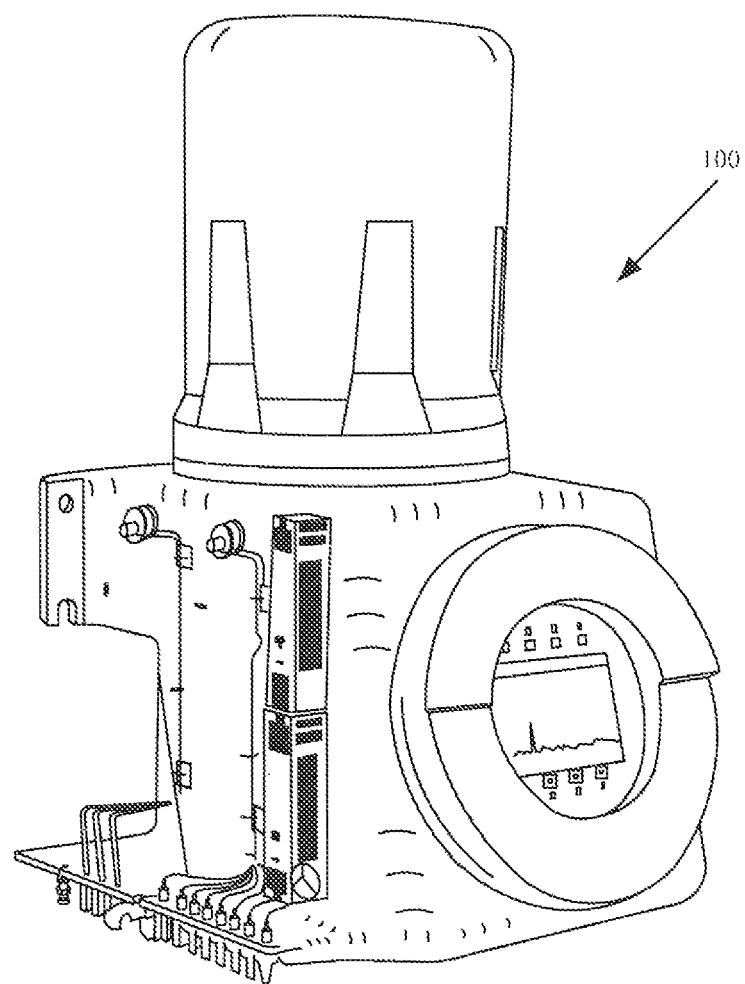
FIGS. 1A-1C illustrate one example of a gas chromatograph with a monitoring component in accordance with one embodiment of the present invention.

Gas analyzers generally measure gas composition in a wide variety of applications. For example, gas chromatographs may be configured to provide information to a technician, such as chromatograms, mole percentages of detected components in an analyzed sample, generated reports and trends. In one embodiment, a gas chromatograph may comprise a MODBUS protocol and/or analog input/output interfaces.

One problem with existing analyzers, such as gas chromatograph units, is the inability for the unit to detect and self-diagnose issues, or to provide an indication to a technician of detected column health, detector functionality, and sample loop functionality after prolonged usage. Therefore, it may be difficult to determine whether a given analyzer component is aging prematurely or has a detectable error or malfunction. Having access to such information may provide a technician with information that can help inform decisions with regard to a gas chromatograph, for example, recommending preemptive replacement or repair for a specific component.

In the example of a gas chromatograph, types of failure may include: column contamination, column deterioration, a column loose connection, and poor installation. Some example indications that may be provided with regard to a detector may include: a detector filament out of balance, a dirty or defective detector, a detector power off state, a blown detector fuse, or detected degradation due to use or wear. Additionally, in one embodiment, a gas chromatograph monitoring component may provide indications with regard to a variety of other issues including, but not limited to: unwanted peaks in a chromatogram, back flush valve port related to port leak, observed baseline noise, water injection, valve noise integration, a peak drift alarm, water in the vent, sample shutoff valve failure, vent blockage, and detected leakage.

In one embodiment, a gas chromatograph is provided with a monitoring component, which may be configured to monitor one or more parameters over time. In one embodiment, the monitoring component is configured to provide an indication of the health of components and subcomponents of the gas chromatograph to a technician. In one embodiment, a gas chromatograph monitoring component may monitor the health of columns, detectors, and the sample loop, as well as associated subcomponents. The monitoring component may be configured to provide an alert to a technician, in one embodiment, in advance of an anticipated component failure, reducing a risk of unanticipated component failure.

In one embodiment, an analyzer monitoring component may integrate expert knowledge and historic data for improved self-diagnosis and fault prediction. For example, the monitoring component may incorporate data regarding known correlation between observable analyzer trends and known component issues. In one embodiment, the analyzer monitoring component is configured to provide a statistics-based monitoring function for components and subcomponents of an analyzer, such as a gas chromatograph. In another embodiment, the monitoring component comprises a fuzzy logic-based hybrid module that analyzes behavior of analyzer parameters over time. Some examples of parameters of interest that are specific to a gas chromatograph include: retention time, area, height, response factors, etc. The fuzzy logic-based hybrid module may, in one embodiment, analyze observed parameters in context with gas chromatograph expert knowledge to diagnose and detect potential component fault in advance, allowing for repair. Monitoring may comprise, in one embodiment, periodic monitoring of gas chromatograph data. In another embodiment, monitoring comprises monitoring each gas chromatograph analysis. The ability to detect and monitor component health may also assist in managing repair and replacement inventory.

Figure 1B:
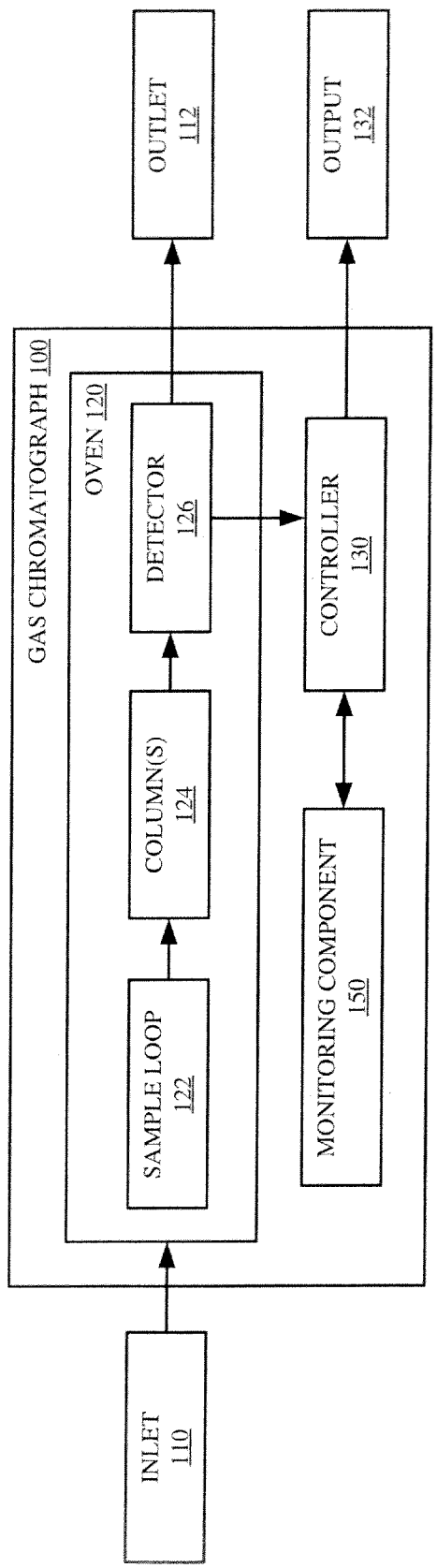
Figure 1C:
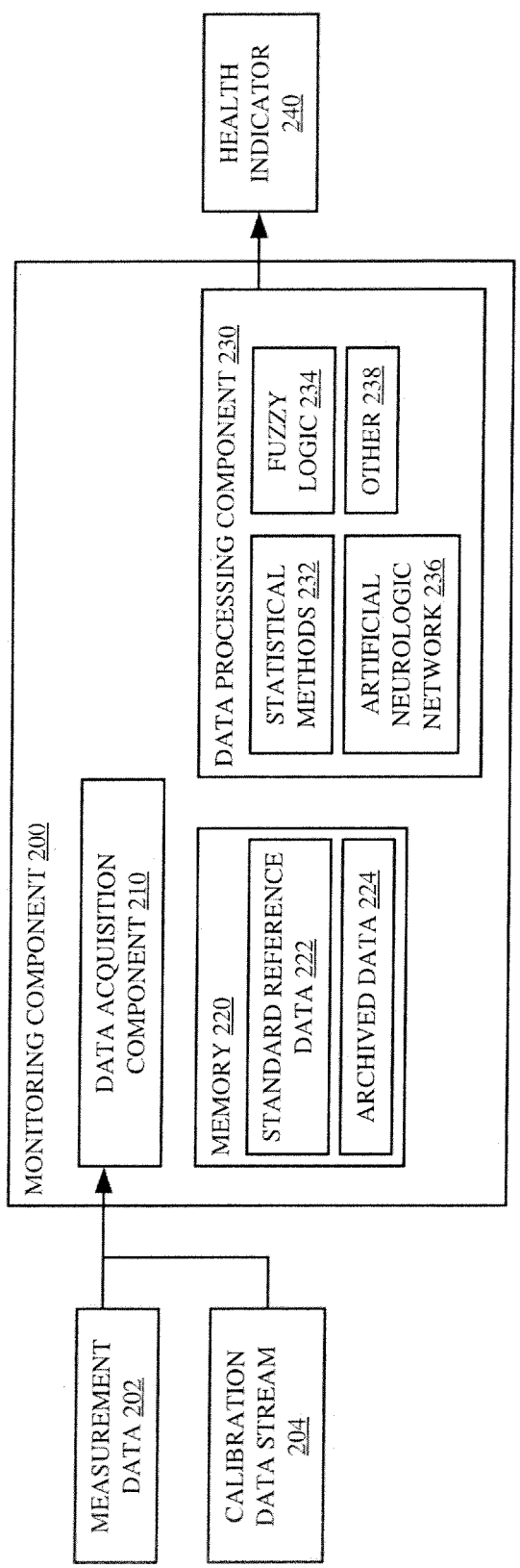

FIGS. 1A-1C illustrate one example of a gas chromatograph with a monitoring component in accordance with one embodiment of the present invention. FIG. 1A illustrates one example embodiment of a gas chromatograph 100 with which embodiments of the present invention may be useful. However, while FIG. 1A illustrates, for example, a model 700XA gas chromatograph, available from Rosemount Analytical Inc., methods and embodiments provided herein may be useful with other exemplary gas analyzers.

FIG. 1B is a diagrammatic system view of a gas analyzer with which embodiments of the present invention may be useful. Gas chromatograph 100 comprises, in one embodiment, one or more inlets 110. Inlet(s) 110 may be configured to allow for suitable sources of carrier gas and sample gas, for example through chromatograph 100, to outlet 112, which comprises appropriate disposal lines, in one embodiment. In one embodiment, carrier gas is provided to a flow panel where it passes through a regulator and dryer before entering analyzer oven 120, where it may pass through a carrier gas preheater coil.

Sample gas enters chromatograph 100, in one embodiment, and passes through a sample loop 122. Both sample gas and carrier gas may, in one embodiment, enter a plurality of pneumatically controlled multi-port selector valves configured to selectively flow various volumes of sample and/or carrier gas through one or more chromatographic columns 124, in accordance with known gas chromatography techniques. Each multi-port selector valve may, in one embodiment, be fluidically coupled to a respective solenoid, which may be configured to receive a control signal from a controller, for example controller 130. In one embodiment, controller 130 is also operably coupled to a detector 126.

In one embodiment, detector 126 is a thermal conductivity detector disposed within analyzer oven 120 and is configured to fully control flow through gas chromatograph 100, for example by virtue of controlling one or more solenoids (not shown). Additionally, in one embodiment, controller 130 is configured to determine the response of detector 126 to gas flow therethrough. In one embodiment, controller 130 selectably introduces the sample into a chromatographic column 124 for a selected amount of time, reverses the flow of gas through column 124, directs the reverse flow through detector 124, and records the response over time.

Controller 130 preferably includes a microprocessor, or other suitable device configured to execute a sequence of instructions to calculate analytic parameters, and store information. Controller 130 may comprise, or may be coupled to, volatile and/or non-volatile memory (shown in FIG. 1C). In one embodiment, controller 130 is configured to provide an audio or visual output 132. Output 132 may be presented on an attached display, user interface, or may be provided to another device for display, e.g. a remote computing unit.

In one embodiment, controller 130 is also coupled to, or comprises, a monitoring component 150. In one embodiment, monitoring component 150 analyzes current gas chromatograph data and compares it to historic data, or known standard data, in order to detect potential deviations in one or more parameters over time, for example retention time, area, etc. Monitoring component 150 may be configured to provide an indication, for example output 132, indicating that one or more components is exhibiting abnormal behavior. In one embodiment, the provided indication specifies a component experiencing abnormal behavior, and suggests a response, for example replacement of a dirty column, defective detector, or solenoid valve, etc.

FIG. 1C provides an illustrative diagrammatic view of a monitoring component 200 in accordance with one embodiment of the present invention. In one embodiment, monitoring component 200 is similar to monitoring component 150 presented and described with respect to FIG. 1B, and provides monitoring and diagnostic indications regarding one or more components of an analyzer, such as a gas chromatograph. Monitoring component 200, in one embodiment, comprises a gas chromatograph data inlet source 202. In one embodiment, gas chromatograph data inlet source 202 includes data from one or more recent gas chromatograph analyses.

In one embodiment, monitoring component 200 also comprises a calibration data inlet stream 204, configured to receive information on one or more recent calibrations of the gas chromatograph. In one embodiment, gas chromatograph inlet data 202 and calibration data stream 204 are provided to a data acquisition component 210 within monitoring component 200. Data acquisition component 210 may serve, in one embodiment, to aggregate incoming information about the gas chromatograph and one or more of its components or subcomponents. Data acquisition component 210 may be coupled to a memory 220, in one embodiment. Memory 220 may be configured to store standard reference data 222, and/or archived data 224. Archive data 224 may comprise data related to previous gas chromatograph analyses, or runs as well as previous calibration data. Additionally, archive data 224 may store one or more known good parameters regarding the gas chromatograph and/or gas chromatograph components or subcomponents.

In one embodiment, monitoring component 200 comprises a data processing component 230. Data processing component 230 may be configured, in one embodiment, to analyze incoming data regarding current status of received analyzer parameters, and compare current parameters to previously taken data, for example, retrieved from memory 220. Data processing component 230 may use one or more of known statistical methods 232, fuzzy logic 234, artificial neurologic network 236, and/or other methods 238 of analyzing the information. Data processing component 230 may be configured to provide a health indicator 240. Health indicator 240 may comprise an indicator regarding overall health of an analyzer, such as a gas chromatograph, as a whole, health of one or more components, or an indication of a possible repair or a replacement strategy for one or more components of the analyzer.

In one embodiment, after the end of every gas chromatograph calibration run, monitoring component 200 will retrieve data, for example from data streams 202 and/or 204, and organize the data within memory 220. Memory 220 may be configured to store data from calibration runs in order to more efficiently process historical data. In one embodiment, data processing component 230 may be configured to retrieve information from memory 220, for example periodically or at the end of every gas chromatograph run, and apply statistical methods in order to identify one or more parameters changing over time. In one embodiment, a control chart may be created or employed relative to one or more parameters, and the control chart may be updated over the lifetime of a chromatograph. Control charts may be helpful, in one embodiment, to identify changing parameters over time. In one embodiment, change may comprise detecting that a parameter is increasing, decreasing, experiencing a level shift upwards or downwards, experience a variance, etc. One example control chart is presented in FIG. 2, described in detail below. Determining the slope of an identified trend may indicate how fast a parameter is deviating over time, which can provide an indication of when an anticipated fault condition may occur. In one embodiment, detecting when an anticipated fault condition may occur may provide sufficient time to order replacement parts, which may reduce requirements for on-hand inventory. In one embodiment, monitoring component 200 may be communicably coupled to a remote inventory system, such that replacement parts can be ordered when a parameter deviation is detected.

Figure 2:
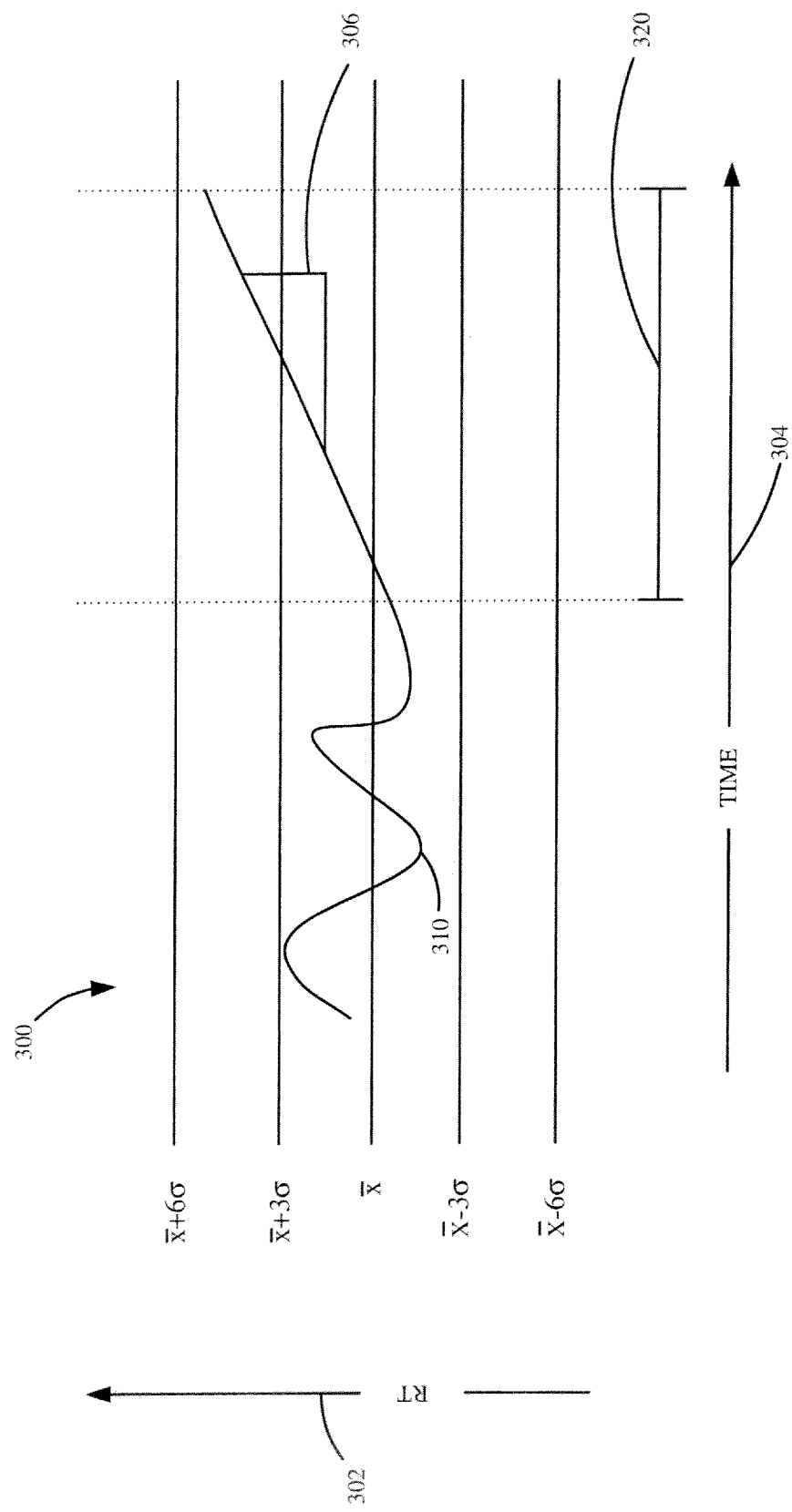
FIG. 2 illustrates an example control chart presenting an experienced retention time of methane deviating over time, in accordance with one embodiment of the present invention.

FIG. 2 illustrates an example control chart presenting an experienced retention time of a component (in this example methane) deviating over time, in accordance with one embodiment of the present invention. In one embodiment, a monitoring component, for example monitoring component 200 is configured to generate a graphical output of a parameter over time. Output 300 may be used, in one embodiment, internally by the monitoring component to detect a deviation, or, in another embodiment, is output to a technician on a display.

Control chart 300 is illustrative of a detected parameter deviation. In one embodiment, only an indication of a detected problem, or indication of a possible solution is presented. For example, in one embodiment, a monitoring component is configured to analyze data from the analyzer over time and detect any deviations that may signal an issue with a component. The monitoring component may then, in one embodiment, determine that the trend corresponds to an anticipated fault of, or a repair need for, one or more components. The monitoring component, in one embodiment, outputs control chart 300 to a technician. The monitoring component may present an indication of an identified trend, an indication of one or more potential problems that may be associated with the identified deviation, and/or an indication of one or more solutions to an identified problem. In one embodiment, monitoring component does not directly output control chart 300, and instead only presents a calculated time to an anticipated component fault. In another embodiment, control chart 300 is illustrative only, such that the monitoring component is configured to only provide an indication to a technician of a proposed solution, for example to replace a column, or to replace a detector fuse, etc.

In one embodiment, control chart 300 comprises raw data corresponding to one or more analyses. Control chart 300 illustratively provides an analysis of retention time 302 for a component (methane) over time 304 for a specific gas chromatograph, for example chromatograph 100.

In one embodiment, a trend line 310 provides an indication of average retention time, x, over time, and indicates whether, and how, the average fluctuates over time, measured in standard deviations, σ. In one embodiment, an area of concern 320 is identified as one where a slope 306 of trend line 310 is increasing over time. The magnitude of slope 306 may provide an indication of how serious a detected problem is. The magnitude of slope 306 may also indicate, or be used to calculate, a lifetime remaining for the gas chromatograph. The remaining lifetime may be useful to calculate when a fault scenario for a particular component is likely to occur. For example, slope 306 may provide an indication that a particular column within the gas chromatograph needs to be replaced in two weeks, for example, or after a specific number of analyses.

However, while FIG. 2 illustratively presents a control chart 300 for one specific parameter, retention time of methane through a gas chromatograph over time, for example, other parameters may also be tracked over time. Tracking multiple parameters over time may allow a monitoring component to determine a full health picture of an analyzer. In one embodiment, tracking multiple parameters of a gas chromatograph over time helps provide an updated health picture of the gas chromatograph and one or more of its components or subcomponents and a warning prior to a fault. Tracking the full health of an analyzer over time may also allow for a monitoring component to provide indications to a technician of times to repair or replace different components, or subcomponents, of the analyzer, such that anticipated faults are avoided. In one embodiment, the monitoring component may also be able to reduce on-hand replacement part inventory requirements, as repair and replacement needs can be more easily anticipated and planned based on detecting parameter deviations early.

In one embodiment, once trends are detected in one or more tracked parameters, the monitoring component is configured to calculate a severity of the problem. For example, if the parameters are changing at a fast rate, it may indicate that the problem is severe, and that remedial action must be taken soon. The degree of severity may be provided by the monitoring component, for example, a qualitative indication, e.g. "severe," or a quantitative indication, e.g. one week left before a component must be repaired or replaced.

FIG. 3 illustrates one example of a Component/Symptom Matrix that may be useful in accordance with some embodiments of the present invention. In one embodiment, one or more control charts, such as those presented in FIG. 2, may, in combination, provide an overall indication of gas chromatograph health. Detecting one or more parameters over time may allow for a monitoring component to provide an indication of an issue by identifying one or more symptoms present and correlating the observed symptoms to possible issues. FIG. 3 provides one example Component/Symptom Matrix 400 that may be used to correlate an identified symptom with a potential issue for a gas chromatograph. For example, an increase in retention time may indicate column contamination. Therefore, detecting that a retention time is increasing may indicate that one or more columns may need to be replaced or repaired due to column contamination.

Another example may comprise detection that a baseline cannot be zeroed. As indicated in Matrix 400, this may correlate to an out-of-balance detector filament. In one embodiment, Matrix 400 is provided to a technician working with a gas chromatograph, such that when a monitoring component provides an indication of a detected symptom, a technician can consult Matrix 400 to determine a potential problem with a gas chromatograph. In another embodiment, Matrix 400 is stored within a memory of the monitoring component, for example memory 220 of module 200. Monitoring component 200, in one embodiment, for example using data processing component 230, compares observed trends in control charts 300 for a plurality of tracked parameters and identifies symptoms 402. Once one or more symptoms 402 are detected, monitoring component 200 may then identify which potential issues 404 may be present, and provide an indication to a technician. For example, some symptoms 402 may correlate to any of: column contamination, defective detector filaments, and/or increase in column bleed. In one embodiment, monitoring component 200 provides an indication of all potential issues, such that the technician must detect which issues are responsible for the observed symptom. In another embodiment, monitoring component 200 provides an indication of the most likely issue, for example by performing a correlation of observed symptoms to determine which issue, or issues, are most likely present. As can be appreciated, other types of analyzers may have a different matrix 400 since various parameters of such analyzers may vary with changes in different components and analyzer conditions.

In one embodiment, knowing how potential symptoms correlate to potential issues, and knowing how quickly observed parameter deviations are occurring, may allow for a gas analyzer monitoring component to predict a lifetime remaining of a gas analyzer, such as a gas chromatograph, or one of its components or subcomponents. This may be done in a variety of ways, and some exemplary methods are described below with respect to FIGS. 4-6.

In one embodiment, expert knowledge regarding how potential symptoms correlate to potential issues is stored within a memory module 220, such that monitoring component 200 can retrieve and apply expert knowledge to identified symptoms to determine which potential issue is most likely responsible for an observed parameter trend. In one embodiment, once an issue is identified as a potential cause for an observed parameter deviation, monitoring component 200 is configured to provide an indication, for example through health indicator 240, of the identified issue.

Figure 4:
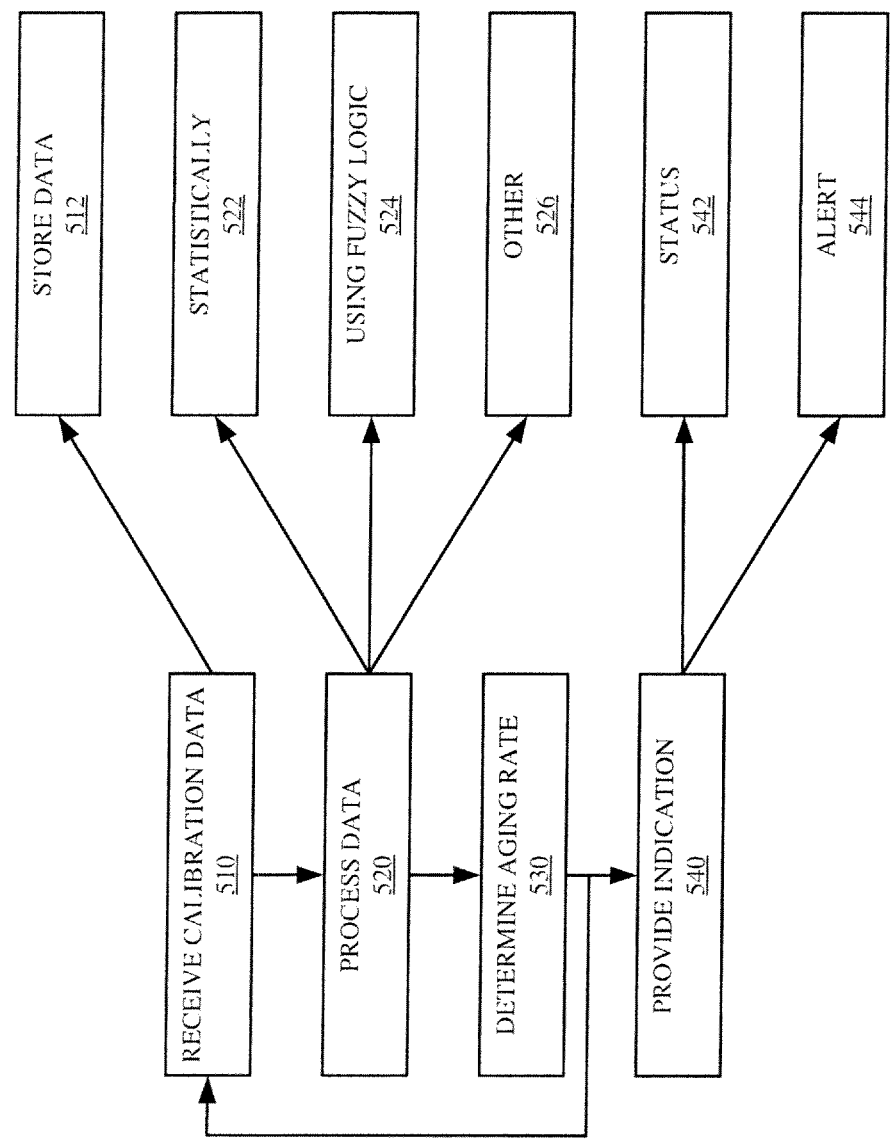
FIG. 4 illustrates a flow diagram of one example method of providing an indication of gas chromatograph health in accordance with one embodiment of the present invention.

FIG. 4 illustrates a flow diagram of one example method of providing an indication of gas analyzer health in accordance with one embodiment of the present invention. Method 500 may be useful for detecting and providing an alert for a detected problem of a gas analyzer. Method 500 may also be used, in one embodiment, to provide a status regarding the gas analyzer and/or one of its components or subcomponents.

In block 510, calibration data is received from a gas analyzer. The received calibration data may be stored, as indicated in block 512, for future analysis, in one embodiment. In another embodiment, received data is analyzed as it is received. In a further embodiment, a monitoring component may conduct periodic analyses, for example based on a time interval, for example weekly or monthly, or after a given number of analyses, for example, once every 10 runs.

In block 520, received calibration data is processed. In one embodiment, processing data comprises comparing recently received data to historical data, known good data, known standard data, etc. Processing data may comprise a statistical analysis, as indicated in block 522, or a fuzzy logic-based analysis, as indicated in block 524, or using another analytical technique, as indicated in block 526. Processing data, as indicated in block 520, may also comprise creating a chart, or otherwise detecting whether or not a parameter deviation is occurring. If a trend is observed, the monitoring component may flag that parameter, in one embodiment. Flagging a parameter may comprise, in one embodiment, noting a potential trend and providing an indication to a technician. In one embodiment, flagging a parameter comprises adjusting an analysis schedule to monitor the detected trend. In one embodiment, processing calibration data comprises associating a detected symptom with an issue and/or with a specific component.

In block 530, the monitoring component determines an age of one or more gas analyzer components. Different components may age faster or slower based on several factors, for example based on a number or type of samples tested. Determining aging may comprise detecting an operational lifetime remaining for one or more components. For example, detecting that a gas chromatograph column is contaminated, and a rate of contamination, may allow a monitoring component to determine the operational lifetime remaining, prior to replacement or repair the column. Age of one or more components may be calculated, in one embodiment, based on a detected parameter deviation. The slope of the detected deviation, in one embodiment, may provide an indication of severity, and a time to fault.

In block 540 an indication is provided. In one embodiment, the indication comprises an alert 544 indicating that one or more components of a gas analyzer needs repair or replacement. Providing an alert 544 may include indicating an estimated time to a fault scenario. In another embodiment, the indication comprises a status 542 of the gas analyzer. Status 542, in another embodiment, may specify a status of one or more components. For example, in one embodiment, providing a status 542 may comprise indicating that a column status is qualitatively 'poor' as opposed to 'good' or 'excellent,' and/or indicating an operational lifetime remaining, for example that a column has less than three more months of operational life before repair or replacement is required.

Method 500 may be useful in order to provide a technician with an indication of when components of a gas chromatograph require replacement or repair. This may help a technician avoid fault scenarios, or detect issues that may not be readily apparent by inspection of a single chromatogram or physical inspection of the gas chromatograph. The ability to process data, using method 500 may keep a given gas chromatograph in better overall health, and identify potential fault issues early.

Figure 5:
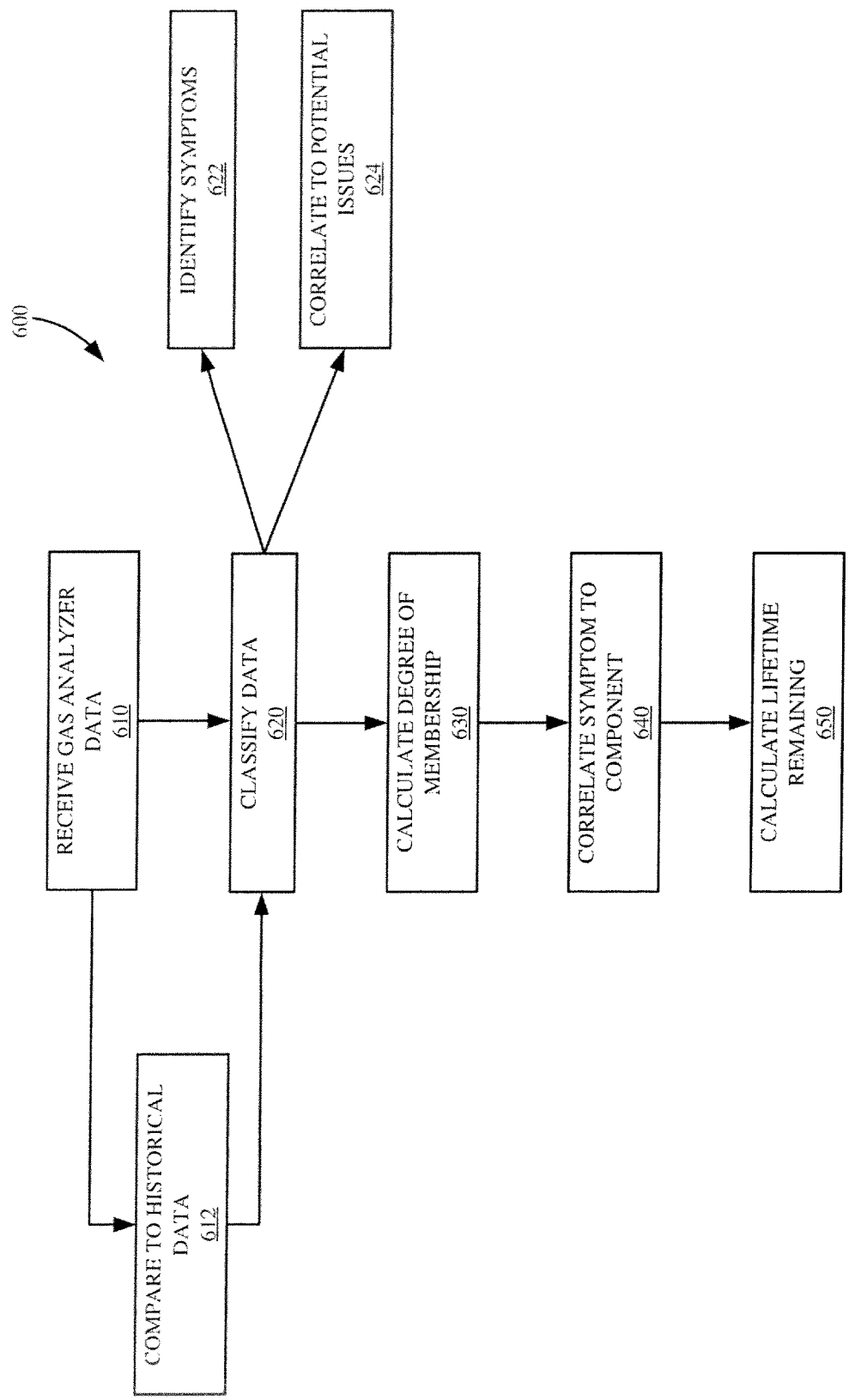
FIG. 5 is a flow diagram of a method for determining a lifetime remaining of a gas chromatograph component in accordance with one embodiment of the present invention.

FIG. 5 illustrates a flow diagram of one example method for determining a lifetime remaining of a gas chromatograph component in accordance with one embodiment of the present invention. Method 600 may be useful to calculate a lifetime remaining for gas chromatograph component. For example, a detected symptom may lead to a fault scenario, or inaccuracy, requiring repair or replacement. Method 600, therefore, may be useful, to provide an alert as a component ages past a desired quality standard, or an alert comprising an estimate of when the component will age past the desired quality standard.

In block 610, in one embodiment, gas analyzer data is received by a monitoring component. In one embodiment, receiving gas analyzer data comprises receiving recent calibration data and/or recent chromatograms.

In block 612, gas analyzer data is compared to historic, or stored, analyzer data. In one embodiment, a comparison is made between known-good and recently obtained data, to determine whether a parameter is trending away from average, and how severely. In one embodiment, a comparison is made against historic data to detect whether a parameter is experiencing a statistically significant drift.

In block 620, gas analyzer data is classified. In one embodiment, classifying data in block 620 comprises identifying potential symptoms 622. Identifying symptoms 622 may comprise the monitoring component generating one or more control charts, for one or more parameters, and identifying any observed deviations, or trends, away from an average. In one embodiment, once an identified trend reaches a significant deviation, for example one or more standard deviations away from average, the trend is classified as a potential symptom. In one embodiment, in addition to identifying a trend, a severity of the symptom is calculated. The severity may be identified, in one embodiment, based on a deviation rate for the observed trend. For a linear trend, the deviation rate corresponds to the slope. For a non-linear trend, the severity may be calculated graphically, by identifying when the trend will pass a threshold corresponding to a fault scenario, for example, or using other methods.

Identified trends may, in one embodiment, be correlated to potential issues associated with a component using a Component/Symptom Matrix, such as that presented in FIG. 3. Classifying data, in block 620 may also comprise identifying potential symptoms, for example based on identified parameter deviations, as indicated in block 622. Issues may be identified, as indicated in block 624, by comparing one or more known symptoms to issues associated with such symptoms, for example using a Component/Symptom Matrix. Identifying potential issues may also comprise comparing collected data in light of analysis from gas chromatograph expert knowledge, which may assist in correlating an identified symptom and an issue.

In block 630, a degree of membership is calculated for each observed trend. The degree of membership may correspond to a length of time since a parameter first deviated, and a deviation rate. In one embodiment, a calculated degree of membership may provide an indication of a severity of a detected issue. If the behavior of one or more parameters is changing at a fast rate, it may indicate that the issue is severe. Conversely, if the parameters are changing at a slow rate, it may indicate that the issue is mild. Knowing a degree of membership, for example calculated in block 630, may allow for a technician, or a monitoring component of a gas analyzer, to determine whether action needs to be taken immediately, or at what time in the future action must be taken to prevent a fault scenario, or unacceptable inaccuracy in chromatograph analyses.

In block 640, in one embodiment, a correlation identifies potential issues, related to one or more components, based on observed symptoms. In one embodiment, the correlation comprises analyzing a confirmability matrix, compiled based on input from one or more gas analyzer experts.

An occurrence matrix may specify how often symptoms occur. A confirmability matrix may be useful to identify how strongly an identified symptom correlates to a problem, for example what degree they are related to each other. For example, multiple symptoms may correlate to a single issue, or one symptom may correlate with multiple issues. For example, multiple symptoms may indicate a column contamination, and a single symptom, for example high background signal noise, may correlate with multiple issues. A confirmability matrix may provide a better indication of how strongly a specific symptom correlates to a specific issue. Once a monitoring component has information regarding symptoms and issue correlation, the monitoring component may perform a composition operation to detect a degree of membership for the correlation.

In block 650, a lifetime remaining is calculated for a gas analyzer component. For example, in the example of control chart 300, where an observed deviation is linear, calculating a remaining lifetime comprises determining a slope, and when an unacceptable level of drift will be surpassed. The unacceptable level of drift may correspond to an unacceptable inaccuracy level, in one embodiment. In another embodiment, the unacceptable level of drift corresponds to a fault scenario for a component.

Method 600 may be useful for a monitoring component of a gas analyzer to calculate a remaining operational lifetime for one or more components of a gas analyzer, or to provide a technician with an indication of anticipated fault. Method 600 may also be useful to quantifiably calculate a lifetime remaining based on observed parameter deviations over time.

Figure 6:
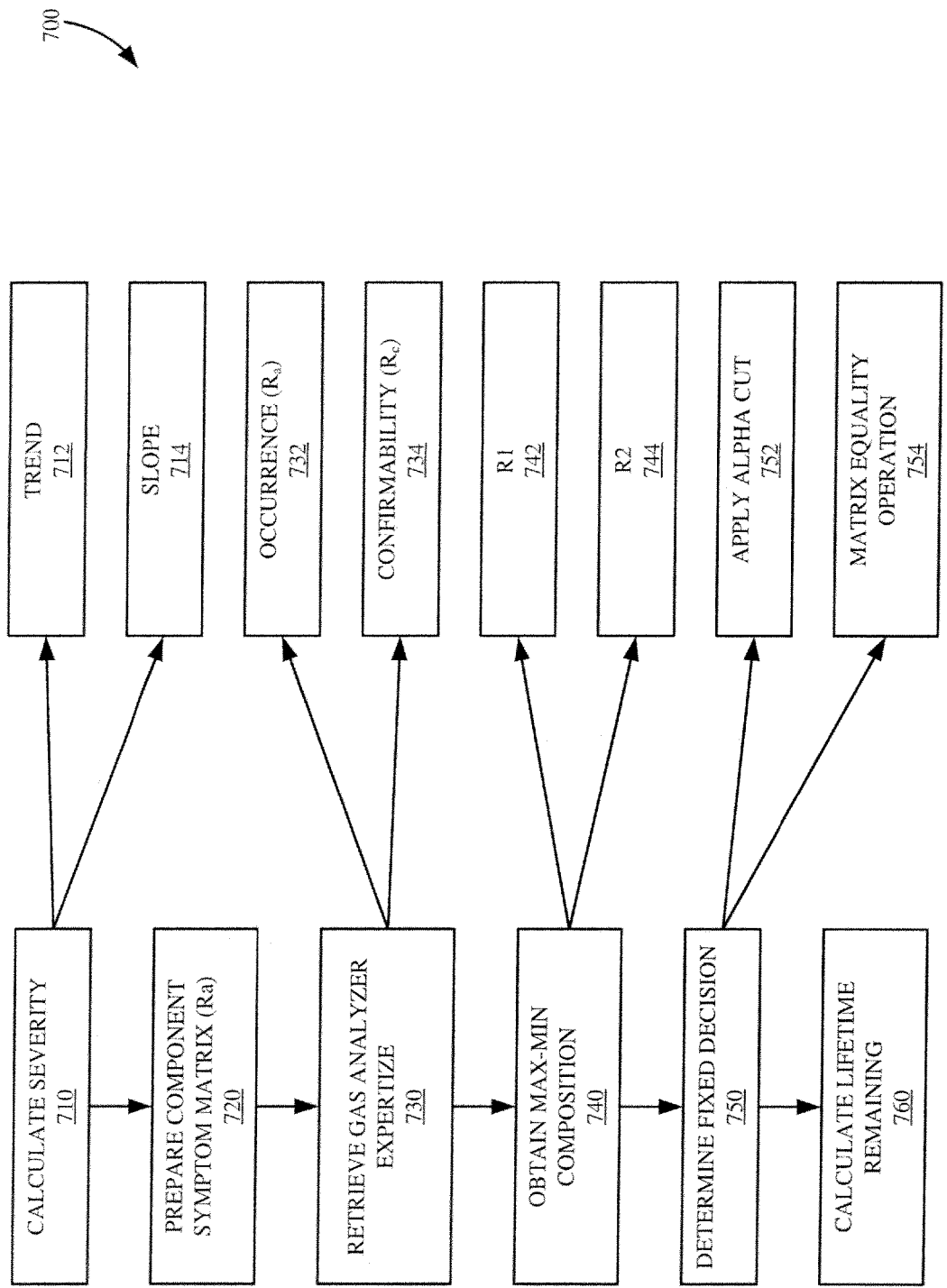
FIG. 6 is a flow diagram of a method for calculating a lifetime remaining of a gas chromatograph component using fuzzy logic in accordance with one embodiment of the present invention.

FIG. 6 illustrates a flow diagram of a method for calculating a lifetime remaining of a gas analyzer component using fuzzy logic in accordance with one embodiment of the present invention. Method 700 may be useful, in one embodiment, to provide a reliable estimated lifetime remaining for a gas analyzer component, which may be useful in planning a repair schedule. Additionally, method 700 may help to reduce or eliminate unexpected fault conditions, and may quickly and accurately isolate responsible components for detected data deficiencies.

Method 700 begins in block 710, where a severity of a detected parameter deviation is calculated. In one embodiment, the severity is calculated by identifying one or more trends 712 for one or more parameters measured by a gas analyzer. The severity of a detected deviation may also be calculated, in one embodiment by determining the slope, or rate of change 714, of trend 712.

In block 720, a Component/Symptom Matrix is obtained. In one embodiment, the component/system matrix, $R_a$, is generated by calculating a maximum between an observed trend 712, and slope 714, and multiplying it by an Issue/Symptom Matrix. The Issue/Symptom Matrix may be similar to that presented in FIG. 3, for example.

In block 730, gas analyzer expertise is retrieved. In one embodiment, gas analyzer expertise comprises an occurrence matrix, $R_o$, and/or a confirmability matrix, $R_c$. The occurrence matrix 732 correlates symptoms to a specific problem and the confirmability matrix 734 indicates how strongly symptoms confirm a specific problem. For example, matrix 734 may indicate how strongly an increased retention time in a gas chromatograph confirms a column contamination problem, or may indicate a different problem altogether.

In block 740, a max-min composition is obtained. In one embodiment, obtaining the max-min composition is accomplished by applying Equation 1, below.

$$\mu_{Component\ Vs\ Issues}(x, z) = \max_{y \in Symptom} (\min(\mu_{Component\ Vs\ Symptom}(x, y), \mu_{Symptom\ Vs\ Issues}(y, z)))$$

EQUATION 1

Where, x∈{Components}, y∈{Symptoms}, z∈{Issues/Problems/Causes}, and μ is the degree of membership. Equation 1 may be useful in order to aggregate expert knowledge with regard to the calculated matrices in order to obtain R1 and R2, using Equations 2 and 3 illustrated below.

$$R1 = R_a \circ R_c$$ EQUATION 2

$$R2 = R_a \circ R_o$$ EQUATION 3

R1 is a composition between $R_a$, the Component/Symptom Matrix, and $R_c$, the confirmability matrix. Similarly, R2 is a composition between the Component/Symptoms Matrix, $R_a$, and the occurrence matrix, $R_o$.

In block 750, a fixed decision is determined. The fixed decision may correspond to a matrix operation resulting in either a 0 or 1 answer. The fixed decision may be useful in order to determine whether a component is functioning effectively, is approaching a fault condition, or is in need of repair. In one embodiment, a fixed decision is achieved by applying an alpha cut, as indicated by block 752. The alpha cut may, for example, be set to 0.5 with respect to x+6σ. Applying the alpha cut on the matrices R1 and R2 may result in a fixed decision, in the form of either 0 or 1. Determining a fixed decision may also be achieved by applying a matrix equality operation, as indicated in block 754. Applying a matrix equality operation may, in one embodiment, provide an alternative mechanism to confirm a fault scenario.

In block 760, once an anticipated fault scenario in confirmed, for example by determining a fixed decision, in one embodiment, an operational lifetime remaining is calculated for the relevant component. For ease of explanation, an example calculation is presented for a detected linear trend. However, a remaining lifetime may also be calculated for detected non-linear deviations. In one embodiment, for a linear trend, a straight line equation is used to calculate an operational lifetime remaining, shown in Equation 4 below.

$$y=mx+c \qquad \text{EQUATION 4}$$

In Equation 4, x represents a time in days remaining, y represents a control warning value, m represents slope, and c represents a constant. Therefore, calculating a time in days remaining can be achieved by rearranging Equation 4 to provide x.

Looking to a linear trend line, such as that shown in FIG. 3 for example, an increasing deviation is observed in a retention time of methane through the gas chromatograph over time. This may indicate, for example, that the column responsible for separating out a methane component is experiencing some contamination. The rate of change, or the observed slope, m, indicates how fast contamination is occurring within the column.

However, simply identifying that contamination is occurring does not necessarily indicate that action, for example, replacement of the contaminated column is required, and when. Therefore, a monitoring component may not immediately provide an alert to a technician, but may provide an indication that it is necessary to observe retention time in the noted column closely. Additionally, an indication may be provided that contamination is occurring, however an alert to replace the column may not be provided until the trend line crosses a warning limit, or a control limit. For example, a warning indication may be provided when a warning limit, for example, a percent contamination threshold of the column, is surpassed. In one embodiment, after detecting that contamination is occurring, a monitoring component may determine a maximum number of days remaining for the contaminated column. This may allow the monitoring component to calculate a contamination rate for the column. This may allow for a degree of membership to be calculated for the identified symptom and the contamination.

A monitoring component may be configured to calculate a lifetime remaining by identifying a trend and calculating when a warning value and a fault value will be surpassed. For example, a linear trend can be identified and a warning value can be calculated using the linear equation presented in Equation 5, where x represents time in days, y represents a control warning value, and m represents slope. The calculation can be repeated for a fault value to determine a lifetime remaining until a fault occurs.

Adding a monitoring component may allow for a gas analyzer to reduce the number of fault occurrences, and improve data accuracy throughout an operational lifetime. Additionally, use of the symptoms and methods herein may allow a technician to take advantage of expert knowledge and make more intelligent decisions concerning prospective fault scenarios. Additionally, use of systems and methods described herein may help to reduce human error in fault diagnoses. Additionally, systems and methods herein may help to provide early warnings and avoid abrupt gas analyzer failures. Additionally, the presence of monitoring component using systems and methods described herein may boost confidence in the results from such a gas analyzer. Additionally, knowing an estimated remaining lifetime may assist in planning for maintenance and avoiding excessive inventory of spare parts on site.

Although the present invention has been described with reference to preferred embodiments, workers skilled in the art will recognize that changes may be made in form and detail without departing from the spirit and scope of the invention. For example, while embodiments of the present invention have been described in terms of a gas chromatograph, embodiments of the present invention are applicable to a wide array of gas analyzers. Further, while embodiments of the present invention herein describe the diagnostic monitoring component as a component of a gas analyzer, such as a gas chromatograph, it is expressly contemplated that the monitoring component may be a remote component that is communicatively coupled to one or more gas analyzers.

What is claimed is:

1. A gas analyzer comprising:
 a sample inlet, configured to receive a sample, coupled to a sample outlet;
 a detector operably disposed between the sample inlet and the sample outlet and configured to provide an indication relative to the sample;
 a microprocessor configured to provide a diagnostic indication regarding the detector of the gas analyzer and provide a fuzzy logic-based module to analyze behavior of gas analyzer parameters over time, and wherein the microprocessor is configured to control flow through the gas analyzer; the microprocessor being operably coupled to the detector to analyze the sample, provide an analytical output and provide the diagnostic indication; and
 wherein the diagnostic indication is based on tracking historic data of parameters of the gas analyzer.

2. The gas analyzer of claim 1, and further comprising at least one gas measurement stage disposed between the sample inlet and the sample outlet.

3. The gas analyzer of claim 1, wherein the diagnostic indication comprises an indication of anticipated fault for the detector of the gas analyzer.

4. The gas analyzer of claim 1, wherein the diagnostic indication comprises an estimated remaining lifetime remaining for the detector of the gas analyzer.

5. The gas analyzer of claim 1, wherein the diagnostic indication comprises a detected issue with the detector of the gas analyzer.

6. The gas analyzer of claim 1, wherein the diagnostic indication comprises a suggested course of action for the detector of the gas analyzer.

7. The gas analyzer of claim 1, wherein the microprocessor is configured to provide a statistics-based monitoring function regarding the detector of the gas analyzer.

8. The gas analyzer of claim 1, wherein the diagnostic indication regarding the detector comprises indicating a detector filament is out of balance.

9. The gas analyzer of claim 1, wherein the diagnostic indication regarding the detector comprises indicating the detector is defective.

10. The gas analyzer of claim 1, wherein the diagnostic indication regarding the detector comprises indicating the detector is dirty.

11. The gas analyzer of claim 1, wherein the diagnostic indication regarding the detector comprises indicating the detector is in a power off state.

12. The gas analyzer of claim 1, wherein the diagnostic indication regarding the detector comprises indicating the detector has degraded.

* * * * *